United States Patent
Paulisch et al.

(10) Patent No.: US 10,441,337 B2
(45) Date of Patent: Oct. 15, 2019

(54) DISTRACTION AND COMPRESSION IN ONE PLIER

(71) Applicant: Stryker European Holdings I, LLC, Kalamazoo, MI (US)

(72) Inventors: Matthias Paulisch, Solothurn (CH); Nicholas Morfing, Nidau (CH); Jakob Kemper, Lo Barnechea (CL); Julien Borgnard, Goven (FR); Benoit Landais, Chateaubourg (FR); Franck Day, St Médard sur Ille (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 234 days.

(21) Appl. No.: 15/130,439

(22) Filed: Apr. 15, 2016

(65) Prior Publication Data

US 2017/0296248 A1    Oct. 19, 2017

(51) Int. Cl.
*A61B 17/88* (2006.01)
*A61B 17/00* (2006.01)
*A61B 17/56* (2006.01)

(52) U.S. Cl.
CPC ........... *A61B 17/8866* (2013.01); *A61B 2017/00407* (2013.01); *A61B 2017/564* (2013.01)

(58) Field of Classification Search
CPC ............ A61B 17/8866; A61B 17/885; A61B 17/1697; A61B 17/2812; A61B 17/2816; A61B 17/282; A61B 17/2833; A61B 17/0206; A61B 17/025; A61B 2017/681; A61B 2017/564; A61B 2017/2837; A61B 2017/2845
See application file for complete search history.

(56) References Cited

U.S. PATENT DOCUMENTS

| | | | |
|---|---|---|---|
| 4,896,661 A | 1/1990 | Bogert et al. | |
| 5,297,538 A | 3/1994 | Daniel | |
| 6,635,072 B1 * | 10/2003 | Ramamurti | A61B 17/2833 606/208 |
| 7,518,069 B2 * | 4/2009 | Alo | G06F 1/16 200/5 R |
| 7,648,508 B2 | 1/2010 | Lutz et al. | |
| 8,142,355 B2 * | 3/2012 | Blain | A61B 17/0206 600/213 |
| 8,444,649 B2 | 5/2013 | Stad et al. | |
| 8,777,953 B1 * | 7/2014 | Khalili | A61B 17/7086 606/86 A |

(Continued)

*Primary Examiner* — Andrew Yang

(74) *Attorney, Agent, or Firm* — Lerner, David, Littenberg, Krumholz & Mentlik, LLP

(57) ABSTRACT

Surgical tools and methods of their use are provided. A surgical tool includes first and second working members, first and second handle arms, a handle post having first and second ends, the second end confronting the second handle arm, and a ratchet coupled to one of the first and second handle arms and engageable with the other of the first and second handle arms. Movement of the first handle arm with respect to the second handle arm causes movement of the first working member with respect to the second working member. A force applied to the handle post causes the first working member to move in a first direction with respect to the second working member. The ratchet is configured to temporarily prevent the first and second working members from moving with respect to one another.

8 Claims, 11 Drawing Sheets

(56) References Cited

U.S. PATENT DOCUMENTS 8,979,866 B2 * 3/2015 Patel .................... A61B 17/025
 606/105
2015/0088144 A1 3/2015 Patel et al.

* cited by examiner

DISTRACTION AND COMPRESSION IN ONE PLIER

BACKGROUND OF THE INVENTION

The present invention relates to surgical tools and methods of using such tools. More particularly, the present invention relates to a surgical compression and distraction tool having working members, handle arms, a ratchet, and a handle post to aid in moving the working members of the tool, as well as the methods associated with using the tools.

Farabeuf clamps or forceps are used to compress a bone fracture, arthrodesis, or osteotomies by interfacing with two screws at the inside of the clamp jaws. The Farabeuf clamp has a ratchet feature on the handle, which can be used to hold the compression of the fracture while the surgeon installs permanent fixation. The most common places to use a Farabeuf clamp is in the Sacroiliac (SI) Joint, in the Iliac Wing, or near the Pectineal line. Additionally, using a k-wire interface, two small bones can be compressed, such as bones in the hand and foot or the phalanges.

A Jungbluth clamp is currently the only reduction instrument that can be used with screws to open a fracture gap. However, the Jungbluth clamp requires a significant amount of space and requires that screws be seated into the instrument, which is often not possible due to difficult access to the surgical site. The Jungbluth clamp does not utilize a ratchet, as it is equipped with a speedlock which does not hold position as well as a ratchet mechanism.

In small- and mini-fragment kits, instruments such as s K-wire clamp and Reduction Forceps are used to compress or distract k-wires. With the K-wire clamp and Reduction Forceps previously used in small joints, multiple clamps were required at one time to effectively distract or compress a joint or fracture line.

Thus, there exists a need for a surgical tool and method of its use that improves upon these shortcomings.

BRIEF SUMMARY OF THE INVENTION

A first aspect of the present invention is a surgical tool including first and second working members, first and second handle arms, a handle post having first and second ends, the second end confronting the second handle arm, and a ratchet coupled to one of the first and second handle arms and engageable with the other of the first and second handle arms. Movement of the first handle arm with respect to the second handle arm causes movement of the first working member with respect to the second working member. A force applied to the handle post causes the first working member to move in a first direction with respect to the second working member. The ratchet is configured to temporarily prevent the first and second working members from moving with respect to one another.

In accordance with other embodiments of the first aspect, the second end of the handle post may be fixedly coupled to the second handle arm, wherein a force applied to the first end of the handle post causes the first working member to move in the first direction with respect to the second working member. The first end of the handle post may extend through the first handle arm. The force may be applied between the first end of the handle post and the first handle arm.

The first end of the handle post may be coupled to the first handle arm, wherein a force applied to the first end of the handle post causes the first working member to move in the first direction with respect to the second working member.

The first handle arm may have a first handle extension, a first end of the first handle extension being coupled to the first handle arm. A second end of the first handle extension may be coupled to the handle post. The force may be applied between the first handle extension and the first handle arm. The first end of the first handle extension may be located proximally with respect to the second end of the first handle extension. The first end of the first handle extension may be located distally with respect to the second end of the first handle extension. The handle post may be movable between a working configuration in which the second end of the handle post is connected to the second handle arm, and a stored configuration in which the entire handle post is disposed between the first handle arm and the first handle extension.

Distal ends of the first and second working members may each be configured to accept a screw, and the distal end of each of the first and second working members may have a first side facing the opposing working member and a second side opposite the first side, and wherein each of the first and second sides of each of the first and second working members is configured to accept a screw. Distal ends of the first and second working members may each be configured to accept a k-wire. The handle post may have a body that extends longitudinally along an axis. The handle post may have a body that extends along a curve. Facing surfaces of the respective first and second working members may have teeth.

When moved in the first direction, the first working member may move away from the second working member. The first and second working members may be pivotally coupled to one another at a junction. The first and second handle arms may be pivotally coupled to one another at the junction. The junction at which the first and second working members are pivotally coupled may be fixed with respect to both the first working member and adjustable with respect to the second working member. The junction at which the first and second working members are pivotally coupled may be fixed with respect to both the first and second working members. Movement of the first handle arm with respect to the second handle arm may cause the first working member to move in a second direction with respect to the second working member. The second direction may be opposite the first direction.

Movement of the first handle arm away from the second handle arm may cause the first and second working members to move apart from one another. Movement of the first handle arm toward the second handle arm may cause the first and second working members to move apart from one another. Pivoting of the first handle arm with respect to the second handle arm may cause movement of the first working member with respect to the second working member.

The ratchet may have a first set of ratchet teeth configured to temporarily prevent the first and second working members from moving toward one another and a second set of ratchet teeth configured to temporarily prevent the first and second working members from moving apart from one another. The first and second sets of ratchet teeth may be on opposite sides of the ratchet, and the ratchet may be rotatable about its axis to allow engagement of one of the first and second sets of ratchet teeth with a pawl. The ratchet may be temporarily fixed in a first position in which the first set of ratchet teeth engage the pawl to temporarily prevent the first and second working members from moving toward one another and in a second position in which the second set of ratchet teeth engage the pawl to temporarily prevent the first and second working members from moving apart from one another. A coupling between the ratchet and the one of the first and second handle arms to which the ratchet is connected may include a ball plunger assembled inside one of the ratchet or the coupled handle arm and a recess on the other one of the ratchet or the coupled handle arm that cooperate to temporarily fix the ratchet with respect to the coupled handle arm. The ratchet may be coupled to one of the first and second handle arms such that it is movable between a working configuration in which the ratchet is engageable with a pawl on the other of the first and second handle arms, and a stored configuration in which the entire ratchet is disposed between the first and second handle arms. The ratchet may be configured to temporarily prevent the first and second working members from moving toward one another.

A second aspect of the present invention is a surgical tool including first and second working members; first and second handle arms, wherein movement of the first handle arm with respect to the second handle arm causes movement of the first working member with respect to the second working member, wherein the first handle arm has a first handle extension, a first end of the first handle extension being coupled to the first handle arm; a handle post having first and second ends, the first end coupled to the first handle arm, the second end confronting the second handle arm, wherein a second end of the first handle extension is coupled to the handle post, wherein a force applied to the first end of the handle post causes the first working member to move in a first direction with respect to the second working member; and a ratchet coupled to one of the first and second handle arms and engageable with the other of the first and second handle arms, wherein the ratchet is configured to temporarily prevent the first and second working members from moving with respect to one another, wherein the handle post is movable between a working configuration in which the second end of the handle post is connected to the second handle arm, and a stored configuration in which the entire handle post is disposed between the first handle arm and the first handle extension.

A third aspect of the present invention is a method of using a surgical tool including the steps of connecting first and second working members of a surgical tool with respective screws or k-wires located in respective bone portions separated by a joint or fracture, moving the bone portions by moving a first handle arm of the surgical tool with respect to a second handle arm of the surgical tool to cause movement of the first working member with respect to the second working member, wherein moving the first handle arm with respect to the second handle arm includes applying a force to a handle post having first and second ends to cause the first working member to move in a first direction with respect to the second working member, the second end of the handle post confronting the second handle arm, and temporarily preventing the first and second working members from moving with respect to one another by engaging a ratchet that is coupled to one of the first and second handle arms and engageable with the other of the first and second handle arms.

In accordance with other embodiments of the third aspect, the step of moving the bone portions may include distracting and/or compressing the bone portions. The step of temporarily preventing the first and second working members from moving with respect to one another may include temporarily preventing the first and second working members from moving toward one another. The method may further include the steps of disengaging the ratchet, compressing the bone portions by moving the first handle arm with respect to the second handle arm to cause the first and second working members to move toward one another, and reconfiguring the ratchet to temporarily prevent the first and second working members from moving apart from one another. The method may further include the step of implanting one or more of a fixation plate and bone screws to immobilize the joint or fracture. In the method, the distal end of each of the first and second working members may have a first side facing the opposing working member and a second side opposite the first side, the step of connecting the first and second working members may include connecting the first and second working members with respective screws at the respective second sides of the first and second working members, and the step of compressing the bone portions may include connecting the first and second working members with the respective screws at the respective first sides of the first and second working members.

The step of moving the bone portions may include the steps of moving a first handle extension away from the first handle arm, a first end of the first handle extension being coupled to the first handle arm, moving the handle post away from the first handle extension, a second end of the first handle extension being coupled to the handle post, and connecting the second end of the handle post to the second handle arm. The step of applying the force to the handle post may include applying the force between the first handle extension and the first handle arm.

The step of applying the force to the handle post may include applying the force between the first end of the handle post and the first handle arm. The method may further include the step of adjusting an adjustable connection of the second working member with respect to a junction of the surgical tool about which the first and second working members are pivotally coupled, wherein a connection of the first working member is fixed with respect to the junction. The step of engaging the ratchet may include the steps of moving the ratchet away from the one of the first and second handle arms to which it is coupled, and engaging the ratchet with a pawl on the other of the first and second handle arms. The method may further include the step of inserting a k-wire in each of the bone portions separated by the joint or fracture.

The method may further include the steps of drilling a hole into each of the bone portions separated by the joint or fracture, and inserting a screw in each of the holes. The method may further include the step of realigning the distracted bone portions. The step of moving the bone portions may include pivoting the first handle arm with respect to the second handle arm. The step of moving the bone portions may include moving the first handle arm away from the second handle arm. The step of moving the bone portions may include moving the first handle arm toward the second handle arm.

The step of temporarily preventing the first and second working members from moving with respect to one another may include engaging a first set of ratchet teeth of the ratchet to temporarily prevent the first and second working members from moving toward one another or engaging a second set of ratchet teeth of the ratchet to temporarily prevent the first and second working members from moving apart from one another. The method may further include rotating the ratchet about its axis to allow engagement of one of the first and second sets of ratchet teeth with a pawl. The method may further include temporarily fixing the ratchet in one of a first position in which a first set of ratchet teeth engage the pawl to temporarily prevent the first and second working members from moving toward one another and a second position in which the second set of ratchet teeth engage the pawl to temporarily prevent the first and second working members from moving apart from one another. The step of temporarily fixing the ratchet may include engaging a ball plunger assembled inside one of the ratchet or the coupled handle arm with a recess on the other one of the ratchet or the coupled handle arm.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
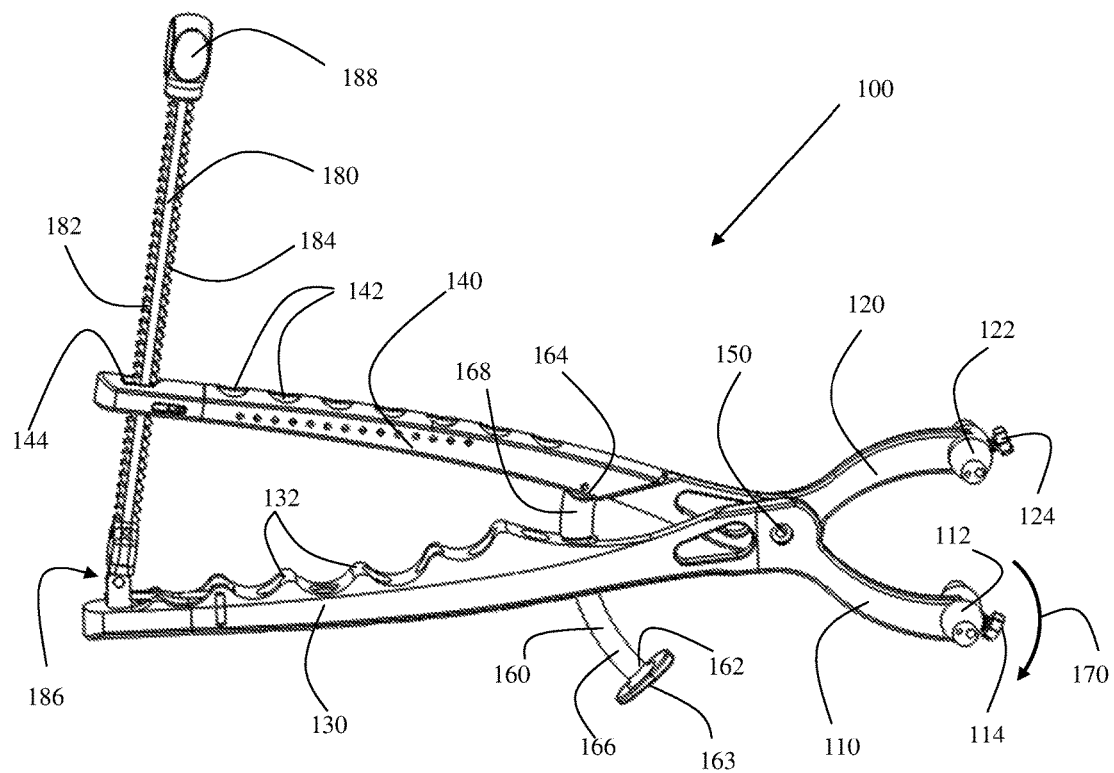
FIG. 1 is a side perspective view of a surgical tool in accordance with one embodiment of the present invention.

Shown in FIG. 1, a first embodiment of a surgical tool 100 includes a first working member 110, a second working member 120, a first handle arm 130, and a second handle arm 140. First and second working members 110, 120 are longitudinal bodies or arms that are pivotally coupled to one another at a junction 150. The longitudinal bodies of first and second working members 110 can be curved, as depicted in FIG. 1, or straight, as shown below in FIG. 2 in connection with surgical tool 200.

Distal ends 112, 122 of first and second working members 110, 120, respectively, are each configured to accept one or more k-wire. As shown in FIG. 1, distal ends 112, 122 are each barrel shaped with a lumen extending therethrough in which a k-wire can be inserted. Locking screws 114, 124 are provided in distal ends 112, 122, respectively, and are configured to extend into communication with the respective lumens to temporarily secure a k-wire. When two k-wires are inserted into a distal end of a working member, different diameter matching with different indications can be proposed, and the bones can be more angularly stable. In other embodiments, the distal ends can each be configured to accept a screw, as described below.

First and second handle arms 130, 140 are also pivotally coupled to one another at junction 150, such that movement of first handle arm 130 with respect to second handle arm 140 causes movement of first working member 110 with respect to second working member 120. Junction 150 can be configured such that the movement between first and second handle arms 130, 140 is pivotal, as in surgical tool 100, or linear in nature. Linear movement could be such that the entire first handle arm moves toward or away from the second handle arm while the structure of the first handle arm remains parallel to the structure of the second handle arm. First and second handle arms 130, 140 can have depressions 142 and/or ridges 132 to facilitate a more secure grip for a user. As shown in FIG. 1, depressions 142 are located on the outer surface of second handle arm 140 and ridges 132 are located on the inner surface of first handle arm 130. Depressions 142 extend through each of first and second handle arms 130, 140 as lumens, as shown for example in FIG. 10.

In surgical tool 100, when first handle arm 130 is moved away from second handle arm 140, first and second working members 110, 120 are caused to move apart from one another. In this way, surgical tool 100 operates in the manner of a conventional wrench. In an alternate embodiment, junction 150 can be configured to cause first and second working members 110, 120 to move apart from one another when first handle arm 130 moved toward second handle arm 140. Also in surgical tool 100, junction 150 is fixed with respect to both first working member 110 and second working member 120. In other embodiments, as further described below, a junction may be adjustable with respect to one or both working members.

Surgical tool 100 includes a handle post 160 having a first end 162 and a second end 164, which confronts second handle arm 140. In surgical tool 100, second end 164 is fixedly coupled to second handle arm 140. This can be a monolithic connection in which handle post 160 and second handle arm 140 are one piece, or it can be a secured connection of separate components, such as by welding, gluing, using a cross-pin, or the like. In other embodiments, other types of couplings or connections between the second end of the handle post and the second handle arm can be utilized, as discussed further below.

First end 162 of handle post 160 extends through a hole or slot in first handle arm 130 and includes a pad 163 that can be accessed by a user to apply pressure to first end 162. As shown in FIG. 1, handle post 160 has a body that extends along a curve in order to allow for handle arms 130, 140 to properly pivot with respect to each other. In other embodiments, the handle post can have a body that extends longitudinally along an axis, in which case the slot through which it extends in first handle arm 130 can be longer. Handle post 160 has a thinner portion 166 adjacent first end 162 and a thicker portion 168 adjacent second end 164. The transition between thinner and thicker portions 166, 168 can be a shoulder that may interface with a corresponding shoulder on first handle arm 130 or the opening therein to provide a limit as to how closely first and second handle arms 130, 140 can be positioned.

A force applied to handle post 160 causes first working member 110 to move in a first direction 170 with respect to second working member 120. Relatively speaking, the force that causes such movement in surgical tool 100 is applied to first end 162 of handle post 160 and between first end 162 and first handle arm 130. That is, a user can grasp first handle arm 130 and press first end 162, for instance, with their thumb. Ridges 132 of first handle arm 130 are provided to enhance the user's grip of first handle arm 130 in this situation. In surgical tool 100, first direction 170 is away from second working member 120 such that applying the force between first end 162 and first handle arm 130 results in a distraction force applied by first and second working members 110, 120. This distraction force can be applied to two bone portions that are respectively connected with first and second working members 110, 120, via k-wires or otherwise.

Surgical tool 100 further includes a ratchet 180 coupled to first handle arm 130 and engageable with second handle arm 140. In other embodiments, this configuration of ratchet 180 and the components with which it interacts may be reversed, in which ratchet 180 is coupled to second handle arm 140 and engageable with first handle arm 130. Ratchet 180 is configured to temporarily prevent first and second handle arms 130, 140, and therefore first and second working members 110, 120, from moving with respect to one another. This can be done in two ways. Ratchet 180 has a first set of ratchet teeth 182 configured to temporarily prevent the first and second working members 110, 120 from moving toward one another and a second set of ratchet teeth 184 configured to temporarily prevent the first and second working members 110, 120 from moving apart from one another. As shown in FIG. 1, first and second sets of ratchet teeth 182 and 184 are on opposite sides of ratchet 180. This allows ratchet 180 to be rotated about its axis at its connection 186 with first handle arm 130 to allow engagement of the appropriate set of ratchet teeth 182 or 184 with a pawl formed on second handle arm 140. This is shown and described in more detail below.

Second handle arm 140 can have an opening 144 through which ratchet 180 extends. In other embodiments such as those described below, the second handle arm can have a forked end. Ratchet 180 has a knob 188 by which a user can rotate or otherwise manipulate ratchet 180. Knob 188 is preferably dimensioned accordingly with opening 144 so that ratchet 180 can be moved to its stored configuration by allowing knob 188 to slide through opening 144.

Ratchet 180 is movable between a working configuration in which it is engageable with a pawl on second handle arm 140 (as shown in FIG. 1), and a stored configuration in which the entirety of ratchet 180 is disposed between first and second handle arms 130, 140. In another embodiment, the ratchet mechanism is fully contained in the handle of the clamp, thereby allowing the ratchet to be switched between distraction and compression modes without removing it from the handle.

Figure 2:
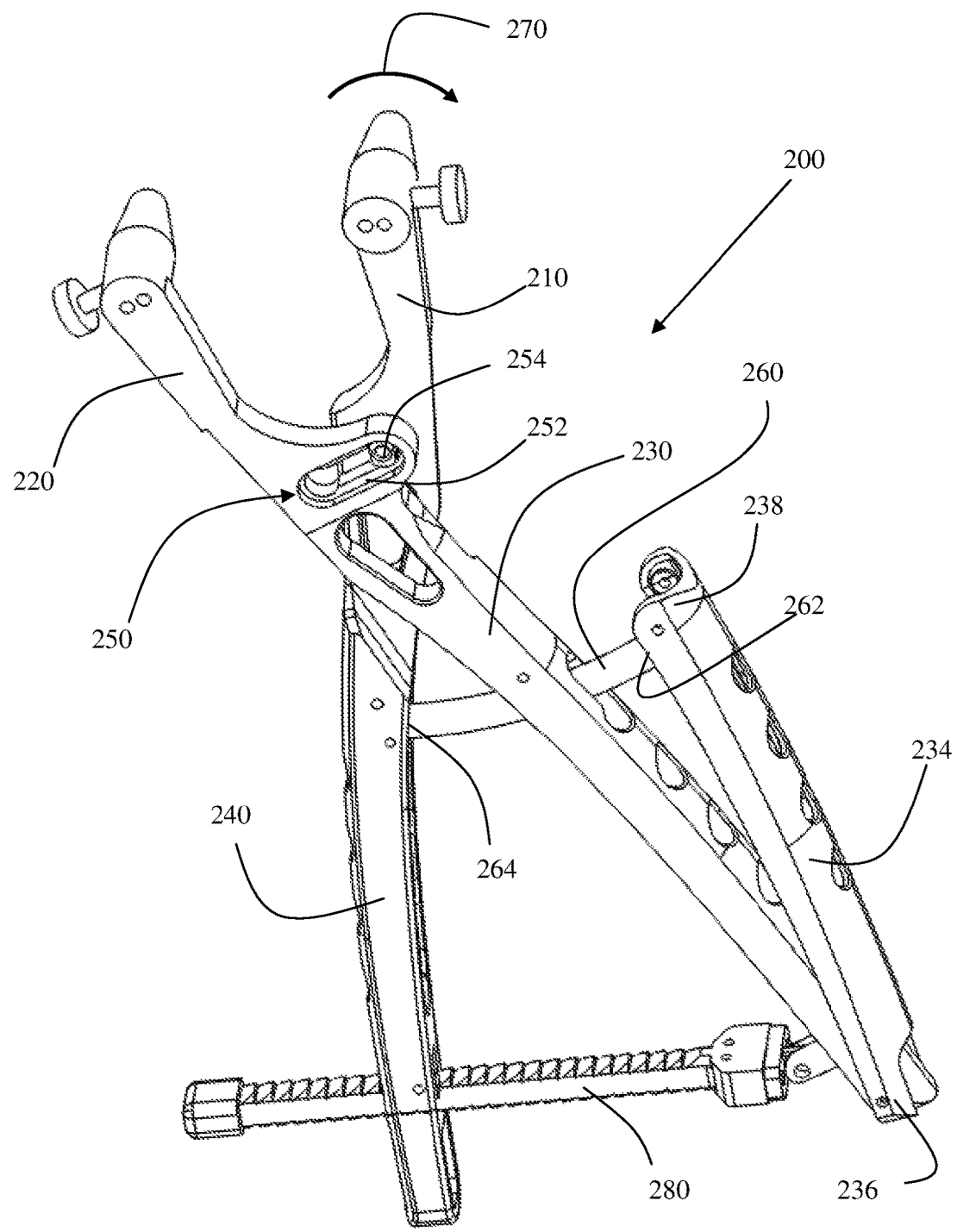
FIG. 2 is a side perspective view of a surgical tool in accordance with another embodiment of the present invention.

A second embodiment of a surgical tool 200 is shown in FIG. 2 and is similar in many respects to surgical tool 100 described above. Surgical tool 200 includes first and second working members 210, 220, first and second handle arms 230, 240, and a ratchet 280. A junction 250 at which first and second working members 210, 220 are pivotally coupled is adjustable with respect to second working member 220. The adjustable junction 250 is facilitated by a slot 252 in second working member 220 and pin 254 in first working member 210 that can move within slot 252, which allows surgical tool 200 to operate similarly to an adjustable wrench so that different separation distances and angles between first and second working members 210, 220 can be achieved.

A handle post 260 has a first end 262 and a second end 264, which confronts second handle arm 240. First end 262 of handle post 260 extends through a hole or slot in first handle arm 230 and is coupled to a first handle extension 234 of first handle arm 230. First handle extension 234 has a first end 236 and a second end 238, which is coupled to handle post 260. In embodiments in which second end 264 of handle post 260 is fixedly coupled to second handle arm 240, first end 262 of handle post is slidably displaceable within second end 238 of first handle extension 234. In embodiments in which second end 264 of handle post 260 is pivotally connected to second handle arm 240, first end 262 of handle post is pivotally connected to second end 238 of first handle extension 234. Both embodiments allow for movements necessary for first handle extension 234 to pivot on first handle arm 230 and operate handle post 260. In configurations in which second end 264 of handle post 260 is connected to second handle arm 240, this connection can be such that second end 264 is placed into contact with second handle arm 240 so that it is touching second handle arm 240 and can be removed simply by moving it away from second handle arm 240. There may be a notch, groove, rib, or other feature in or on second handle arm 240 to aid in maintaining second end 264 at a particular location of second handle arm 240. This type of connection is non-permanent and removable so that second end 264 can be moved into and out of contact with second handle arm 240. On the other hand, in configurations in which second end 264 of handle post 260 is fixedly coupled to second handle arm, this type of coupling is permanent and non-removable. Such a coupling can be a fixed, static coupling such as a monolithic, glued, welded, or other similar connection. In other embodiments, the fixed coupling could be pivotable such as by a pin or hinge connection or the like.

First end 236 of first handle extension 234 is pivotally coupled to first handle arm 230 via a pin or other mechanism and is located proximally with respect to second end 238. A force applied to handle post 260 causes first working member 210 to move in a first direction 270 with respect to second working member 220. In surgical tool 200, the force that causes such movement is applied to first end 262 of handle post 260 and is applied between first handle extension 234 and first handle arm 230. That is, a user can press first handle extension 234 toward first handle arm 230 by holding only these two elements.

Handle post 260 is movable between a working configuration in which second end 264 is connected to second handle arm 240, and a stored configuration in which the entirety of handle post 260 is disposed between first handle arm 230 and first handle extension 234.

Figure 3:
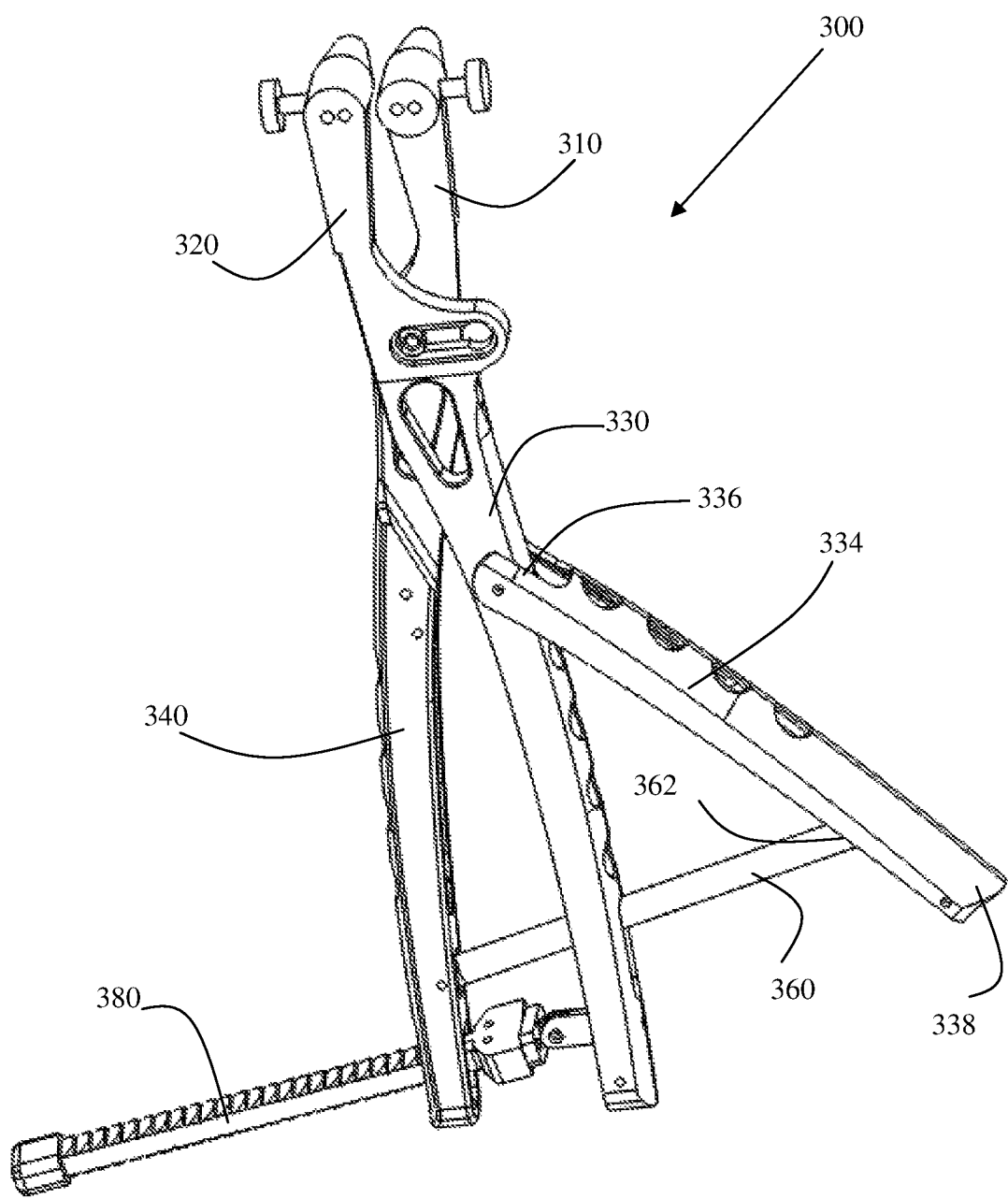
FIG. 3 is a side perspective view of a surgical tool in accordance with another embodiment of the present invention.

A third embodiment of a surgical tool 300 is shown in FIG. 3 and is very similar to surgical tool 200 described above. Surgical tool 300 includes first and second working members 310, 320, first and second handle arms 330, 340, and a ratchet 380. A handle post 360 has a first end 362 connected to a first handle extension 334 of first handle arm 330. First handle extension 334 has a first end 336 and a second end 338, which is coupled to handle post 360. First end 336 of first handle extension 334 is pivotally coupled to first handle arm 330 and is located distally with respect to second end 338. Of course, the connection of first handle extension 334 need not be at the actual end thereof, though it is located adjacent second end 338.

A fourth embodiment of a surgical tool 400 is shown in FIGS. 4-8. Surgical tool 400 includes first and second working members 410, 420 and first and second handle arms 430, 440. First and second working members 410, 420 are pivotally coupled to one another at a junction 450. First and second handle arms 430, 440 are also pivotally coupled to one another at junction 450, such that movement of first handle arm 430 with respect to second handle arm 440 causes movement of first working member 410 with respect to second working member 420. First and second working members 410 are relatively straight bodies that each extend at an acute angle with respect to first and second handle arms 430, 440. That is, when positioned in contact with each other first and second working members 410, 420 extend from junction 450 in a direction that is not parallel to the angle at which first and second handle arms 430, 440 extend from junction 450.

Figure 4:
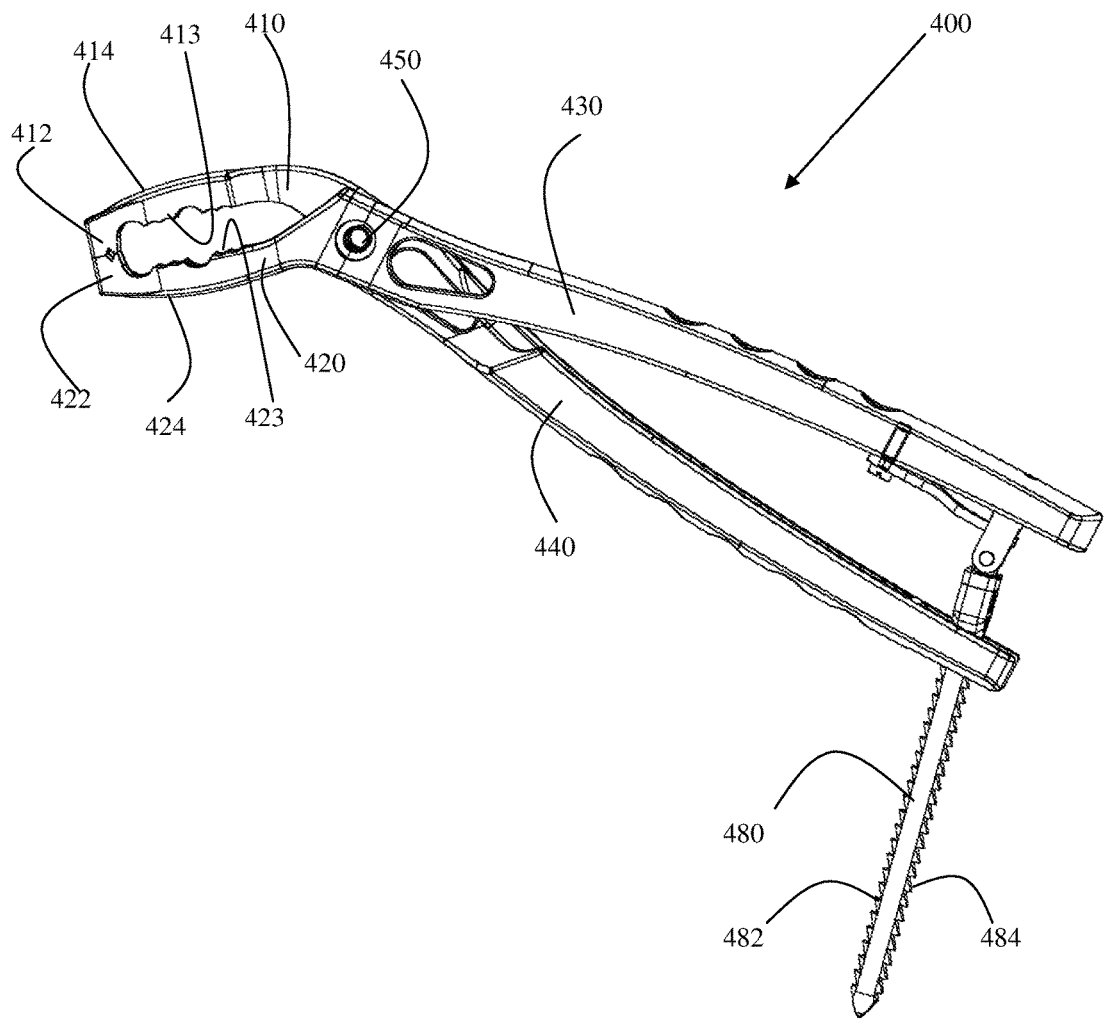
FIG. 4 is a side perspective view of a surgical tool in accordance with another embodiment of the present invention.

Surgical tool 400 operates like a typical wrench. As shown in FIG. 4, a force moving first and second handle arms 430, 440 toward one another causes first and second working members 410, 420 to move toward one another. Likewise, a force moving first and second handle arms 430, 440 apart from one another causes first and second working members 410, 420 to move apart from one another. In another embodiment, junction 450 can be configured such that a force moving first and second handle arms 430, 440 toward one another causes first and second working members 410, 420 to move apart from one another, and vice versa.

Figure 5:
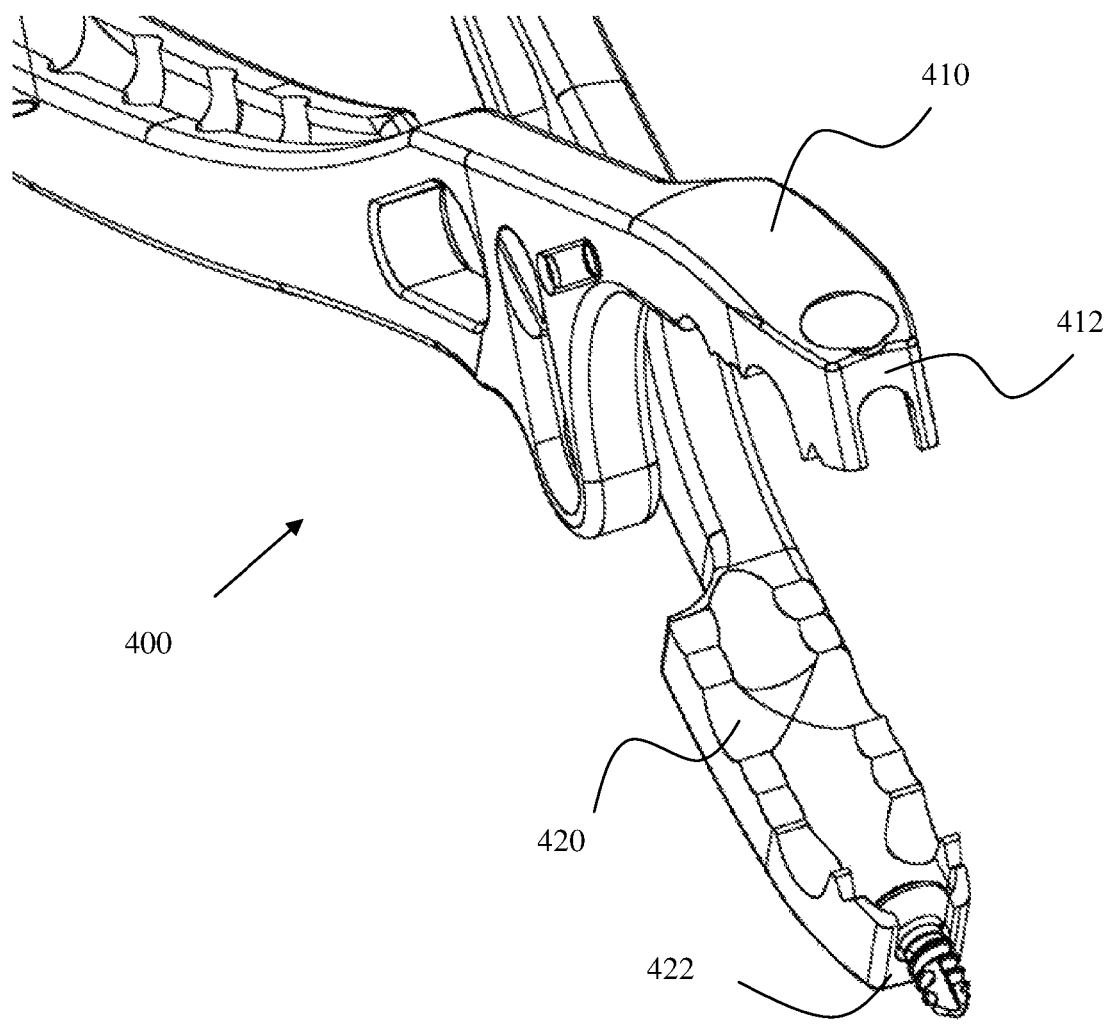
FIG. 5 is a distal perspective view of the working members of the surgical tool shown in FIG. 4.

Distal ends 412, 422 of first and second working members 410, 420, respectively, are each configured to accept a screw, as shown in FIG. 5. Each of distal ends 412, 422 has a first side 413, 423 facing the opposing working member and a second side 414, 424 opposite first side 413, 423. Each of first and second sides 413, 414, 423, 424 of each of first and second working members 410, 420 is configured to accept a screw. That is, as will be described in greater detail below in connection with the method of using surgical tool 400, each of first and second working members 410, 420 is configured to engage a screw at its respective first side 413, 423 when tool 400 is used to compress said screws toward one another. Likewise, each of first and second working members 410, 420 is configured to engage a screw at its respective second side 414, 424 when tool 400 is used to distract said screws away from one another. First sides 413, 423 also have teeth for enhancing a grip on an item when tool 400 is used like a wrench.

Surgical tool 400 includes a ratchet 480 coupled to first handle arm 430 and engageable with second handle arm 440. Ratchet 480 is like those described above, and some elements are shown in greater detail in FIGS. 6-8 with the understanding that those details are also part of the ratchets of the other embodiments disclosed herein. In surgical tool 400, second handle arm 440 has forked ends 449 between which ratchet 480 extends. This allows ratchet 480 to be pivoted out of its engagement with second handle arm 440 without having to open first and second handle arms 430, 440 wide enough to slip ratchet 480 through an opening in second handle arm 440.

Ratchet 480 is configured to temporarily prevent first and second working members 410, 420 from moving with respect to one another. Ratchet 480 has a first set of ratchet teeth 482 configured to temporarily prevent the first and second working members 410, 420 from moving toward one another and a second set of ratchet teeth 484 configured to temporarily prevent the first and second working members 410, 420 from moving apart from one another. Ratchet 480 can be pivoted and rotated about its connection 486 with first handle arm 430 to allow engagement of the appropriate set of ratchet teeth with a pawl 446 formed on second handle arm 440.

Figure 6:
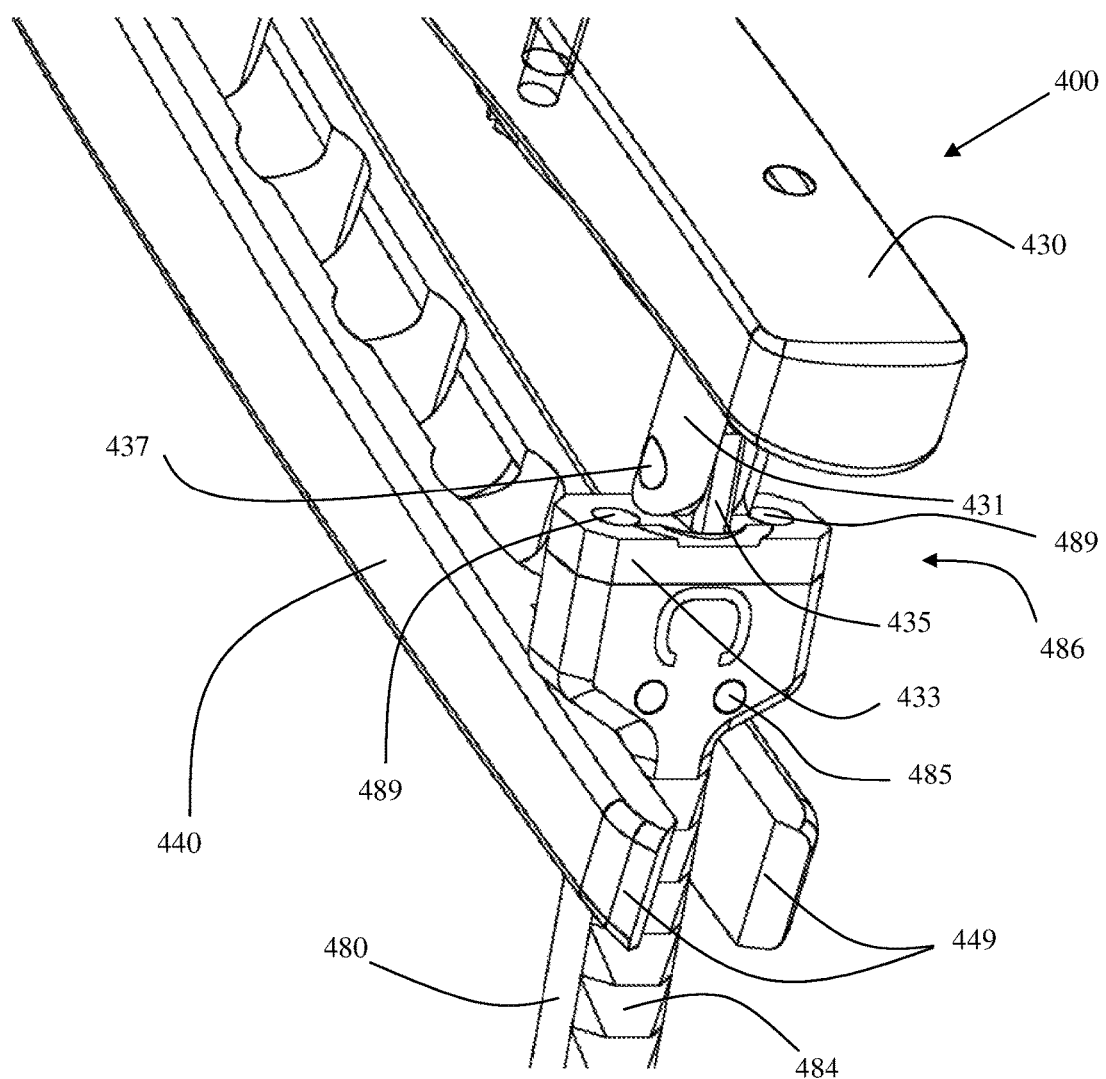
FIG. 6 is a proximal perspective view of the ratchet and handle arms of the surgical tool shown in FIG. 4.
Figure 7:
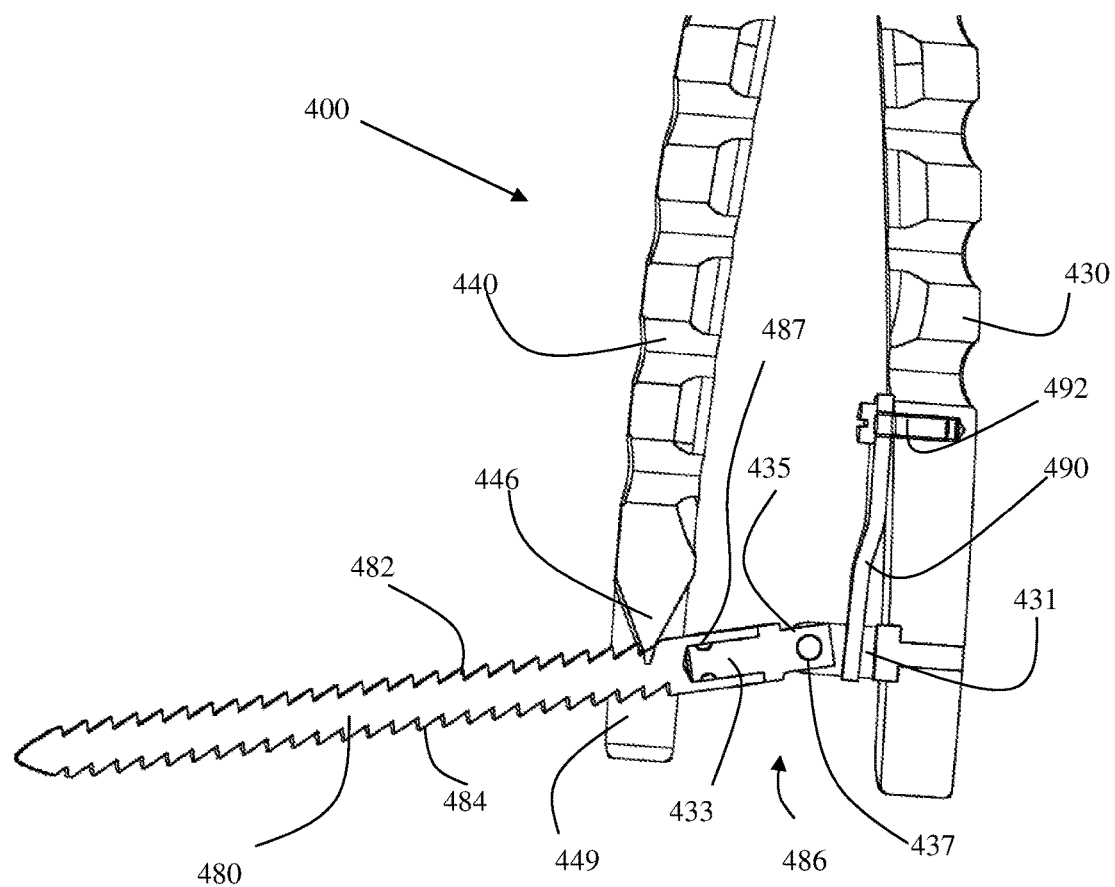
FIG. 7 is a side sectional view of the ratchet and handle arms of the surgical tool shown in FIG. 4.
Figure 8:
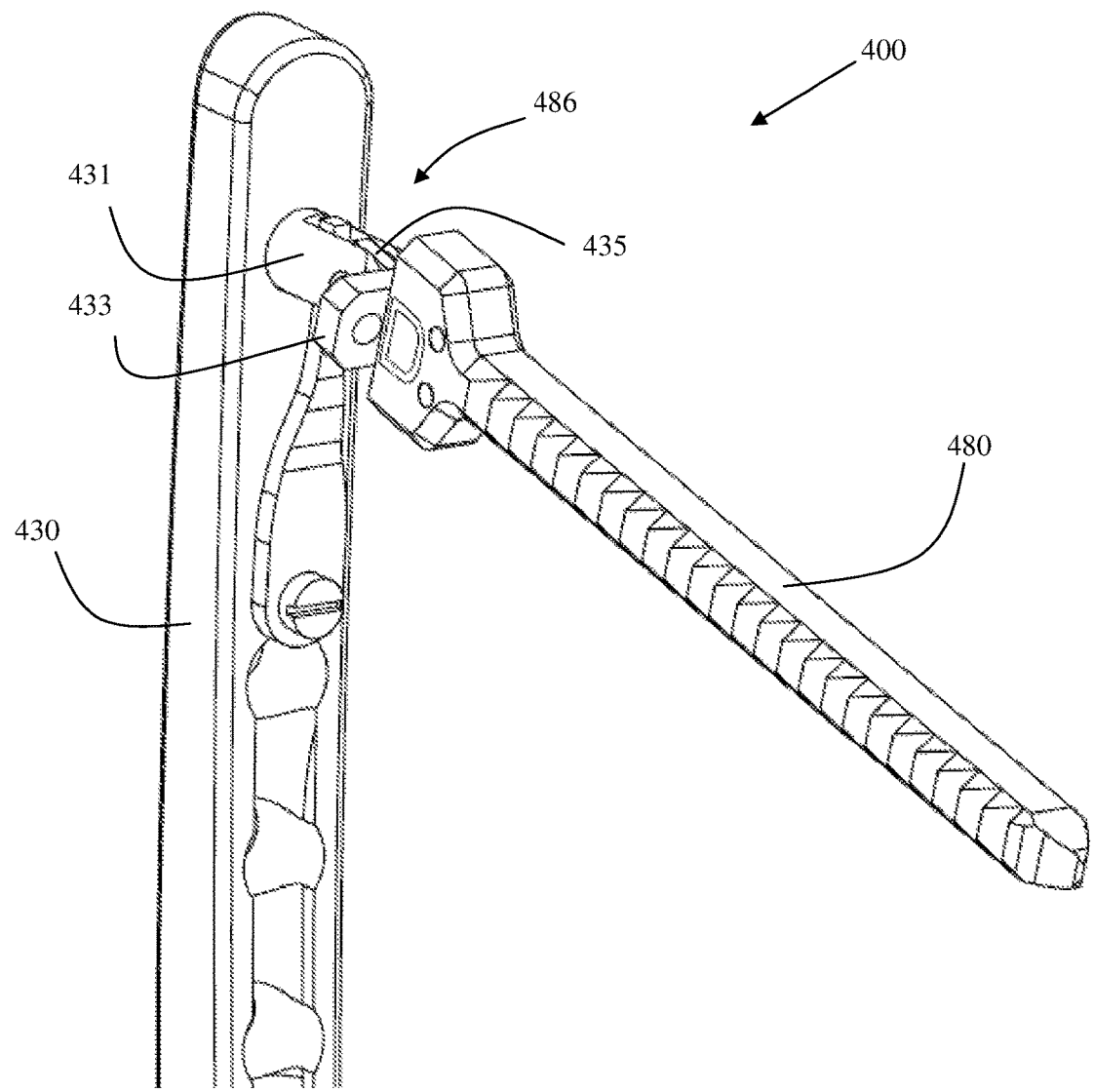
FIG. 8 is another proximal perspective view of the ratchet and a handle arm of the surgical tool shown in FIG. 4.

In its working configuration, ratchet 480 engages pawl 446, as shown in FIG. 7. In its stored configuration, the entirety of ratchet 480 can be disposed between first and second handle arms 430, 440. Connection 486 between ratchet 480 and first handle arm 430 includes a post 431 on first handle arm 430 that is connected to a post 435 of a ratchet cap 433 via a pin 437. Ratchet 480 is rotatably connected with ratchet cap 433, as shown in FIG. 7. Holes 489 on ratchet cap 433 provide recesses that cooperate and engage with ball plungers (not shown) that are assembled inside the mating portion of ratchet 480 to allow ratchet 480 to be temporarily rotationally fixed in either compression mode or distraction mode. Ratchet cap 433 includes two indents 487 (as shown in FIG. 7) that engage assembly pins 485 (as shown in FIG. 6) to connect ratchet 480 to ratchet cap 433. Thus, ratchet 480 can pivot with respect to first handle arm 430 via the axis of pin 437. Ratchet 480 can also rotate about its longitudinal axis through its rotatable connection with ratchet cap 433. This allows for a user to easily move and manipulate ratchet 480 during a selection between first and second sets of ratchet teeth 482, 484 and/or between the working and stored configurations of ratchet 480. Thus, ratchet 480 can extend through a full range of motion from first handle arm 430.

A leaf spring 490 such as a lamellar spring is anchored to first handle arm 430 via a screw 492. Leaf spring 490 is configured to bias ratchet 480 towards pawl 446 to provide a constant force that forces ratchet teeth 482, 484 into pawl 446.

Figure 9:
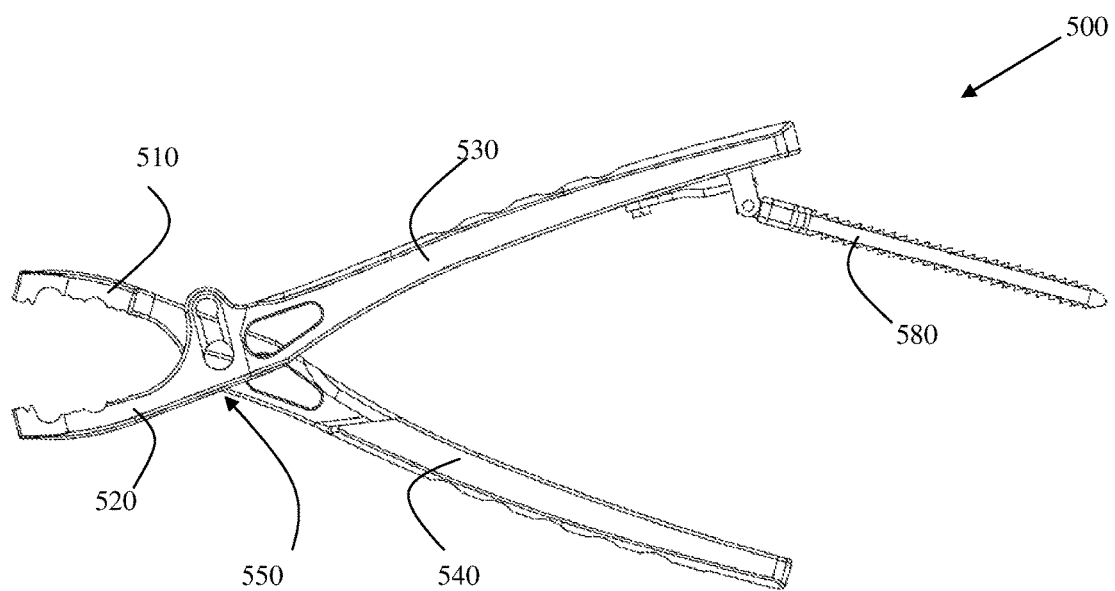
FIG. 9 is a side perspective view of a surgical tool in accordance with another embodiment of the present invention.

A fifth embodiment of a surgical tool 500 is shown in FIG. 9 and is very similar to surgical tool 400 described above. Surgical tool 500 includes first and second working members 510, 520, first and second handle arms 530, 540, and a ratchet 580. First and second working members 510 are each relatively aligned with respect to first and second handle arms 530, 540, as opposed to being angled as in surgical tool 400. A junction 550 at which first and second working members 510, 520 are pivotally coupled is adjustable with respect to second working member 520. The adjustable junction 550 is similar to junction 250 described above.

Figure 10:
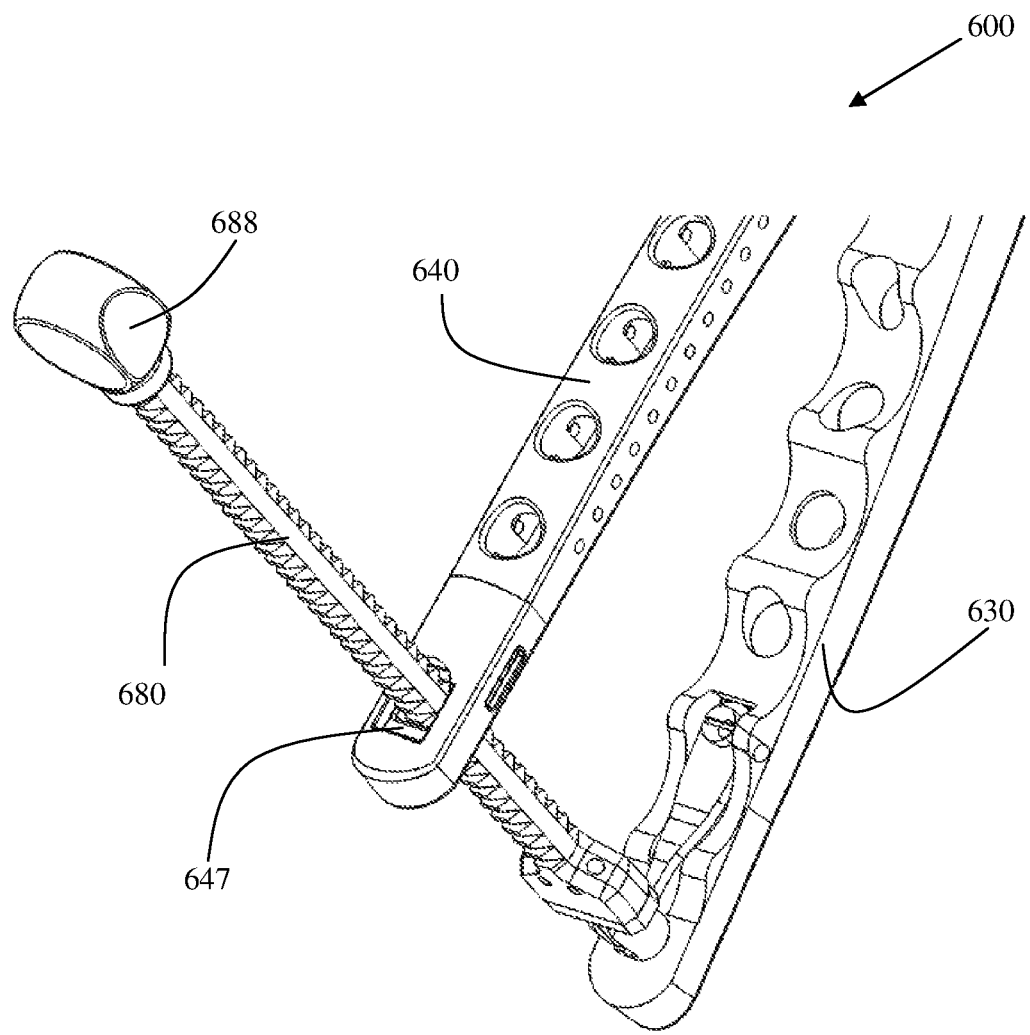
FIG. 10 is a proximal perspective view of a ratchet and handle arms of a surgical tool in accordance with another embodiment of the present invention.
Figure 11:
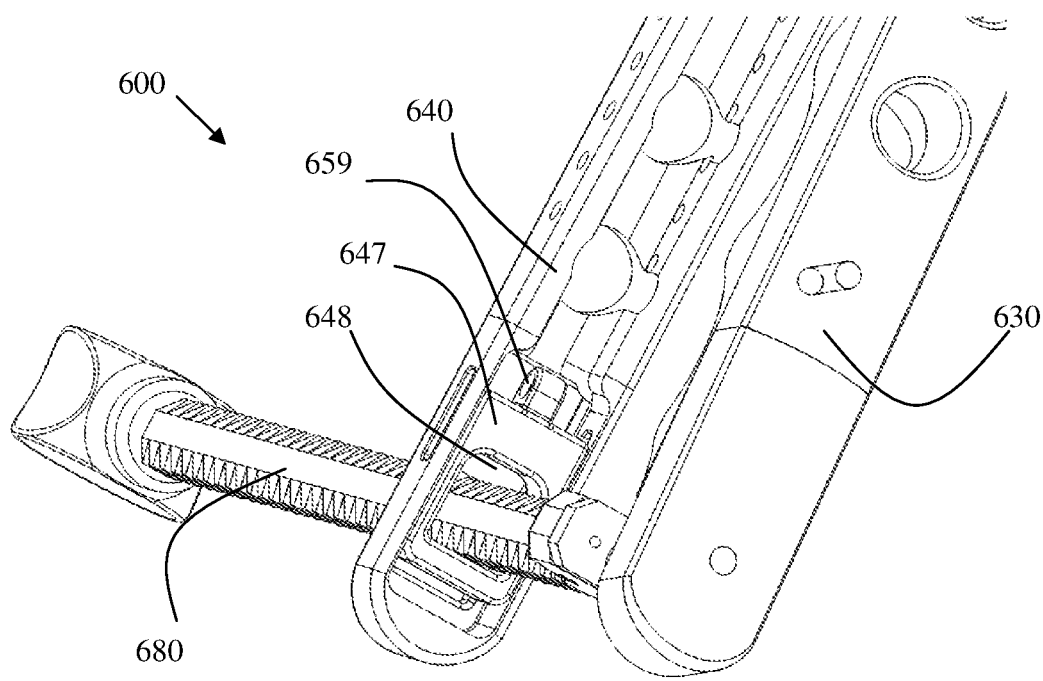
FIG. 11 is another proximal perspective view of the ratchet and handle arms of the surgical tool shown in FIG. 10.
Figure 12:
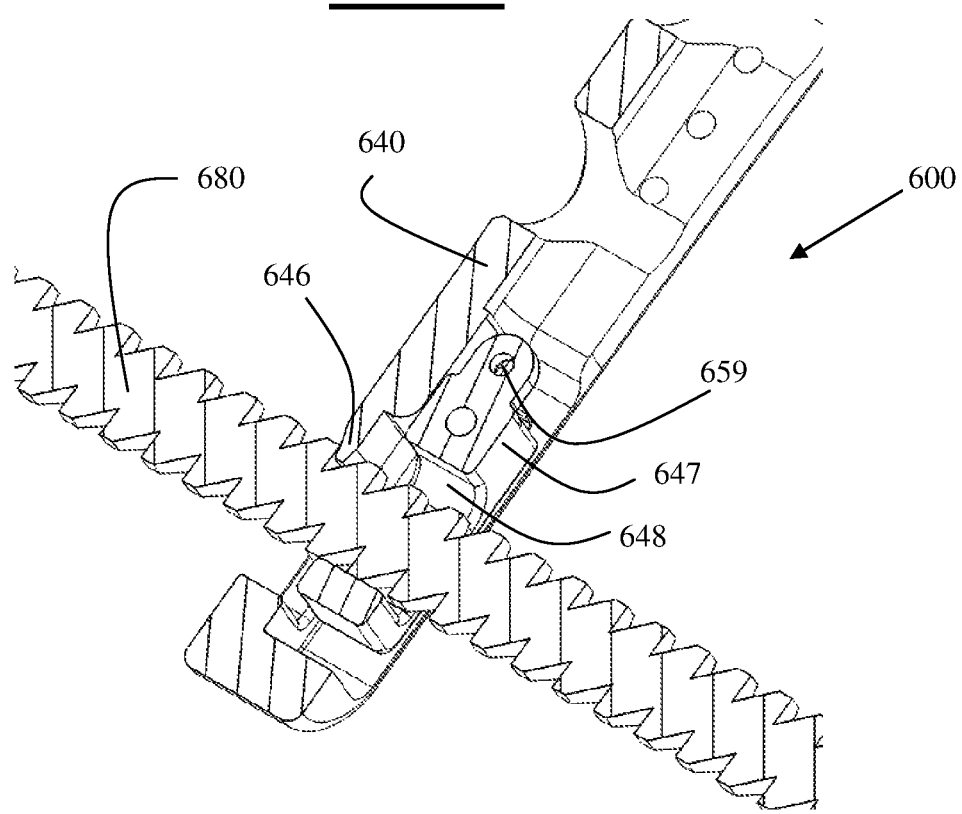
FIG. 12 is a side sectional view of the ratchet and a handle arm of the surgical tool shown in FIG. 10.

As shown in FIGS. 10-12, a sixth embodiment of a surgical tool 600 includes a different pawl mechanism. Surgical tool 600 includes first and second handle arms 630, 640 and a ratchet 680. Second handle arm 640 includes a shuttle 647 having a window 648 through which ratchet 680 is disposed. Second handle arm 640 includes a pawl 646 located adjacent its outer surface. Shuttle 647 is biased by a spring (not shown) into a position toward the working members of surgical tool 600. That position is shown more clearly in FIG. 12 and results in shuttle 647 forcing or maintaining ratchet 680 into engagement with pawl 646. In the configuration shown in FIG. 12, ratchet 680 enables free reduction of the distance between first and second handle arms 630, 640, while preventing an increase of this distance. The spring and shuttle 647 allow the user to move ratchet 680 out of engagement with pawl 646 so that the separation distance between first and second handle arms 630, 640 can be changed. Thereafter, the spring and shuttle 647 maintain ratchet 680 in the new position. Ratchet 680 can also be pulled away from pawl 646 in order to disengage it from pawl 646 and enable free motion of second handle arm 640. Ratchet 680 can be rotated by 90 degrees about its longitudinal axis in order to present a toothless surface thereof toward pawl 646 so that ratchet 680 is effectively disengaged, leading to free motion of second handle arm 640. As indicated above, from the position shown in FIG. 12, ratchet 680 can be rotated by 180 degrees about its longitudinal axis in order to reverse its function and enable free increase of the distance between first and second handle arms 630, 640, while preventing reduction of this distance.

The spring can be connected between an aperture 659 of shuttle 647 and another anchor point on second handle arm 640. Alternatively, the spring can be connected at an anchor point on second handle arm 640 with its opposing end having a pawl to engage ratchet 680. The spring-loaded shuttle 647 can act as an on-off switch for ratchet 680. The user can fix shuttle 647 in place in an open position to allow free passage of ratchet 680. The user can then release shuttle 647 to provide the spring loaded bias for locking the distance between arms 630, 640. Ratchet 680 has a knob 688 by which a user can rotate or otherwise manipulate ratchet 680. When ratchet 680 is in its distraction mode, knob 688 can be pressed with the user's finger to produce the distraction force. Alternatively, in a configuration in which a ratchet mechanism is built into a threaded rod instead of a post having a rectangular cross section, a knob such as knob 688 can be a threaded nut that can be turned around the rod to provide distraction or compression, akin to a speedlock mechanism.

The features of the above described embodiments can be interchanged among different surgical tools. For example, any of the present embodiments may be configured to accept a k-wire or screw at the distal end of either or both of its working members. Likewise, a fixed or adjustable junction could be employed in any of the present embodiments. The location of different connections can also be adjusted to fit a particular desired configuration as long as the functionality of such feature is maintained.

A method of using a surgical tool will now be described in relation to each of surgical tools 100, 200, 300, 400, 500, and 600. Surgical tool 100 will mainly be referenced below with the understanding that the other embodiments operate similarly unless otherwise noted.

During the method of use, access is gained to a joint or fracture site, such as in an ankle of a patient. A k-wire (or a screw as discussed below) can be inserted into each of two bone portions that are separated by a joint or fracture in order to prepare the surgical site for use with a surgical tool as provided herein. First and second working members 110, 120 of surgical tool 100 are connected with respective k-wires by threading the k-wires through lumens in each of first and second working members 110, 120. Locking screws 112, 114 can be tightened to temporarily secure the k-wires in the lumens.

When screws are utilized instead of k-wires, the surgical site preparation can include drilling a hole into each of the bone portions and inserting a screw into each. The first and second working members, such as of surgical tools 400 and 500, are then connected with the screws. The working members can be fitted for a 3.5 mm screw, but an interface to 4.5 mm screws or k-wires of various diameters are contemplated. When the bone portions are intended to be distracted, this includes engaging each screw with a respective second side 414, 424 of first and second working members 410, 420. Alternately, when the bone portions are intended to be compressed, this includes engaging each screw with a respective first side 413, 423 of first and second working members 410, 420.

The surgical method further includes moving the bone portions connected to surgical tool 100 by moving or pivoting first handle arm 130 with respect to second handle arm 140 to cause movement of first working member 110 with respect to second working member 120, and therefore movement of the bone portions. In surgical tool 400 (as in surgical tool 500), moving the bone portions includes moving first and second handle arms 430, 440 toward or apart from one another. In surgical tool 100 (as in surgical tools 200 and 300), moving the bone portions includes applying a force to handle post 160 to cause first working member 110 to move in first direction 170 with respect to second working member 120, which distracts the bone portions. The force is applied between first end 162 of handle post 160 and first handle arm 130, which can be done with one hand. More specifically, in surgical tools 200 and 300, this includes moving first handle extension 234, 334 away from the respective first handle arm, moving handle post 260, 360 away from the respective first handle extension, and connecting the respective second end of handle post 260, 360 to the respective second handle arm. The force is then applied between first handle extension 234, 334 and the respective first handle arm. In surgical tools 100, 200, and 300, moving the bone portions toward one another includes moving first and second handle arms 430, 440 toward one another by applying a force therebetween. The respective handle post can be disconnected during such use, or the user can simply grasp the first and second handle arms and not the first handle extension.

Further in the method, ratchet 180 is engaged to temporarily preventing first and second working members 110, 120 from moving with respect to one another. When surgical tool 100 is used for distraction, this includes temporarily preventing first and second working members 110, 120 from moving toward one another. When ratchet 180 is needed or before the surgical procedure begins, it can be moved from a stored position to a working position in which it is configured to engage a pawl on second handle arm 140.

Once ratchet is used for maintain the tool in distraction and the associated surgical operations are completed, the method can then include disengaging ratchet 180 and compressing the bone portions by moving first handle arm 130 with respect to the second handle arm 140 to cause first and second working members 110, 120, and thus the bone portions, to move toward one another. Ratchet 180 can be reconfigured to temporarily prevent first and second working members 110, 120 from moving apart from one another during this step or afterward. Once the final desired positioning of the bone portions is achieved, a fixation plate and/or one or more bone screws can be implanted to immobilize the joint or fracture.

During the method, use of embodiments such as surgical tool 200 that include an adjustable junction 250 can involve manipulating junction 250 to achieve different and perhaps more desirable separation distances and/or angles between first and second working members 210, 220.

In another exemplary method, access is gained to the fracture site. A k-wire is inserted in each bone portion, or a hole is pre-drilled on each side of the fracture into which 3.5 mm screws are inserted. The working arms of a surgical tool are connected with the screws or k-wire and the bone portions are distracted. The ratchet is placed in distraction mode so that the distracted position can be maintained when pressure is removed from the handle arms. This can be done with one hand of the user, particularly when using one of surgical tools 100, 200, and 300 that include a handle post. In that case, with the ratchet in distraction mode, pressure can be applied between the first handle arm and the handle post, or if present, the first handle extension. In other embodiments, the handle arms can simply be moved apart. Once the joint or fracture is appropriately distracted, it can be cleaned and realigned. The ratchet is then disengaged and the working members can be allowed to close by slowly releasing pressure on the surgical tool handle portion, thereby allowing the joint or fracture site to close. At this point, if screws are inserted in the bone portions, the surgical tool can be placed back on the screws as a clamp, that is, on the outside of the screws. The ratchet is switched into compression mode without removing it from the handle so that the compressed position can be maintained when pressure is removed from the handle arms. This can be done without removing the ratchet from the handle arms by rotating the ratchet about its axis so that the opposing set of ratchet teeth confront the pawl. The joint or fracture can then be compressed with the ratchet engaged. A fixation plate and/or screws can then be implanted to immobilize the joint or fracture, and the surgical tool removed. Use of the surgical tools described herein allow for the joint or fracture to be distracted, cleaned and realigned, and compressed, all while using one single tool that can be more easily manipulated.

As described above, the present surgical tools are embodiments of a device that can easily be placed over screws or wires, that can apply and maintain distraction while repairing or debriding a gap between bone portions, and that can quickly be switched to compression, all with the same device. The tools reverse the mechanism of operation of the clamps. Instead of being used only for compression on the inside of the working members or clamp jaws, the tool can interface with screws on the outside of the working members, allowing the surgeon to distract the fracture. The ratchet mechanism can also be switched to distraction mode, which allows the surgeon to keep the fracture distracted for cleaning and reduction. This allows the surgeon to open a fracture site to allow him to clear the fracture site of bone fragments or soft tissues. It also allows him to correctly align the fracture components before determining his approach and method of fixation. It is particularly useful when used to reduce the SI joint via an anterior approach. The surgical tools require considerably less space to use and therefore, less access to the fracture site.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A surgical tool comprising:
  first and second working members;
  first and second handle arms, wherein movement of the first handle arm with respect to the second handle arm causes movement of the first working member with respect to the second working member;
  a handle post having first and second ends, the second end of the handle post being coupled to the second handle arm and the first end of the handle post extending through the first handle arm, wherein a force applied to the first end of the handle post causes the first working member to move in a first direction with respect to the second working member;
  a first handle extension having first and second ends, the first end of the first handle extension being coupled to the first handle arm and the second end of the first handle extension confronting the first end of the handle post such that the first handle arm is positioned between the second handle arm and the first handle extension; and
  a ratchet coupled to one of the first and second handle arms, wherein the ratchet is engageable with the other of the first and second handle arms and configured to temporarily prevent the first and second working members from moving with respect to one another.

2. The surgical tool of claim 1, wherein the second end of the handle post is fixedly coupled to the second handle arm, wherein a force applied to the first end of the handle post causes the first working member to move in a first direction with respect to the second working member.

3. The surgical tool of claim 1, wherein distal ends of the first and second working members are each configured to accept a screw, and the distal end of each of the first and second working members has a first side facing the opposing working member and a second side opposite the first side, and wherein each of the first and second sides of each of the first and second working members is configured to accept a screw.

4. The surgical tool of claim 1, wherein the ratchet has a first set of ratchet teeth configured to temporarily prevent the first and second working members from moving toward one another and a second set of ratchet teeth configured to temporarily prevent the first and second working members from moving apart from one another.

5. The surgical tool of claim 4, wherein the first and second sets of ratchet teeth are on opposite sides of the ratchet, and the ratchet is rotatable about its axis to allow engagement of one of the first and second sets of ratchet teeth with a pawl.

6. The surgical tool of claim 5, wherein the ratchet can be temporarily fixed in a first position in which the first set of ratchet teeth engage the pawl to temporarily prevent the first and second working members from moving toward one another and in a second position in which the second set of ratchet teeth engage the pawl to temporarily prevent the first and second working members from moving apart from one another.

7. The surgical tool of claim 6, wherein a coupling between the ratchet and the one of the first and second handle arms to which the ratchet is connected includes a ball plunger assembled inside one of the ratchet or the coupled handle arm and a recess on the other one of the ratchet or the coupled handle arm that cooperate to temporarily fix the ratchet with respect to the coupled handle arm.

8. A surgical tool comprising:
  first and second working members;
  first and second handle arms, wherein movement of the first handle arm with respect to the second handle arm causes movement of the first working member with respect to the second working member, wherein the first handle arm has a first handle extension, a first end of the first handle extension being coupled to the first handle arm;

a handle post having first and second ends, the first end coupled to the first handle arm, the second end confronting the second handle arm, wherein a second end of the first handle extension is coupled to the handle post such that the first handle arm is positioned between the second handle arm and the first handle extension, wherein a force applied to the second end of the first handle extension causes the first working member to move in a first direction with respect to the second working member; and a ratchet coupled to one of the first and second handle arms, wherein the ratchet is engageable with the other of the first and second handle arms and configured to temporarily prevent the first and second working members from moving with respect to one another, wherein the handle post is movable between a working configuration in which the second end of the handle post is connected to the second handle arm, and a stored configuration in which the entire handle post is disposed between the first handle arm and the first handle extension.

* * * * *